United States Patent [19]

Heimerl et al.

[11] Patent Number: 5,011,492
[45] Date of Patent: Apr. 30, 1991

[54] SELF-ADHESIVE WOUND SUTURE PLASTER

[75] Inventors: Albert Heimerl, Hamburg; Dietrich Schulte, Pinneberg; Gabriela Götz, Hamburg; Reiner Leutz, Reinbek, all of Fed. Rep. of Germany

[73] Assignee: Biersdorf AG, Hamburg, Fed. Rep. of Germany

[21] Appl. No.: 207,998

[22] Filed: Jun. 17, 1988

[30] Foreign Application Priority Data

Oct. 23, 1987 [DE]  Fed. Rep. of Germany ....... 3735894
Mar. 19, 1988 [DE]  Fed. Rep. of Germany ....... 3809348

[51] Int. Cl.⁵ ..................... A61B 17/04; A61L 15/00
[52] U.S. Cl. ..................... 606/215; 128/156
[58] Field of Search ..................... 128/156; 606/215

[56] References Cited

U.S. PATENT DOCUMENTS

| | | | |
|---|---|---|---|
| 114,750 | 5/1871 | Battersby | 606/215 |
| 2,472,009 | 5/1949 | Gardner | 606/215 |
| 4,173,131 | 11/1979 | Pendergrass et al. | 128/156 |
| 4,207,885 | 6/1980 | Hampton et al. | 128/156 |
| 4,215,684 | 8/1980 | Westip | 128/156 |
| 4,236,550 | 12/1980 | Braun et al. | 128/156 |
| 4,366,814 | 1/1983 | Riedel | 128/156 |
| 4,367,732 | 1/1983 | Poulsen et al. | 128/156 |
| 4,370,981 | 2/1983 | Sanderson | 606/215 |
| 4,742,826 | 5/1988 | McLorg | 128/155 |

FOREIGN PATENT DOCUMENTS 230373  7/1987  European Pat. Off. .
2081177  2/1982  United Kingdom .

Primary Examiner—Stephen C. Pellegrino
Assistant Examiner—Gary Jackson
Attorney, Agent, or Firm—Sprung Horn Kramer & Woods

[57] ABSTRACT

Self-adhesive wound suture plaster with a carrier material, especially in strip form, of an elastic knitted or woven fabric, sheet or nonwoven, which is characterized in that the carrier strip extends under the action of a pulling force and, after this action of force has ended, virtually returns completely to the original length.

Preferably, the carrier strip undergoes a length extension of between about 2 and 10% under the action of a pulling force of 5 N/cm, a length extension of between about 5 and 15% at 10 N/cm and a length extension of between about 15 and 30% at 20 N/cm.

6 Claims, No Drawings

SELF-ADHESIVE WOUND SUTURE PLASTER

BACKGROUND OF THE INVENTION

(1) Field of the Invention

The invention relates to a self-adhesive wound suture plaster with an elastic carrier material.

(2) Description of Related Art

Wound suture plasters are used for closing or fixing skin lesions. They consist in general of a strip-shaped carrier material which is coated wholly or partially with an adhesive composition, and, when they are used, they are stuck across the wound in order to hold the edges of the wound together. The intended result is that, in contrast to stitched wound edges, hardly any visible scars remain after complete healing.

As carrier materials for such wound suture plasters, the most diverse woven fabrics, nonwovens or sheets have hitherto already been proposed or used. Some of these materials, on the one hand, may be adaptable and highly permeable to air and water vapour but are unyielding, such as, for example, according to German Utility Model No. 7,032,197, and some are, on the other hand, made to be elastic and very yielding during the wound healing process, such as, for example, according to European Published Application No. 28,452, European Published Application No. 230,373 and German Offenlegungsschrift No. 3,524,315.

Although these elastic wound closure strips of polyurethane sheet, embossed nonwoven or polymer material cut at an angle to the main stretching axis yield plastically during the healing process of a wound, which process is as a rule characterized by a more or less extensive swelling of the tissue due to oedema formation, and thus prevent damage to the tissue caused by undue compression, their tensioning force is too low to ensure closure of the wound in an optimum manner. After the swelling has subsided, an undesirably wide scar forms as a rule over the wound fissure region as a result of the plastic extension of these products.

It was the object of the invention to develop a wound suture plaster which completely adapts itself to the physiological healing process of a scar and, at any time during this process, ensures tension-free but firm cohesion of the edges of the wound.

SUMMARY OF THE INVENTION

This object is achieved by a wound suture strip with an elastic carrier material, which is characterized in that it extends under the action of a pulling force and, after this action of force has subsided, virtually returns completely to the original length.

This means that, although it elastically yields to a sufficient extent during the swelling of the tissue, it also follows again the shrinking, usual during the progressing healing process, because of its reversible extensibility.

DESCRIPTION OF PREFERRED EMBODIMENT

Preferably, this reversible elasticity which, when measured, represents a hysteresis curve which wholly or at least almost wholly returns to its point of origin, is adjusted such that the wound suture strip undergoes a length extension of between about 1 and 15% under the action of a pulling force of 5 N/cm, a length extension of between about 2 and 20% at 10 N/cm and a length extension of between about 6 and 35% at 20 N/cm.

Those products have proved to be particularly suitable which undergo an extension of between about 2 and 10% at 5 N/cm, between about 5 and 15% at 10 N/cm and between about 15 and 30% at 20 N/cm width (measured on a conventional tensile testing machine at various pulling rates (between 20 and 300 mm/minute) and strip widths from 0.4 to 2.6 cm width). Such extension values are markedly below the extension values of elastic dressings, bandages and even plasters, such as are normally used in medical practice. The values are even so low that the material appears to be hardly elastic in a simple pulling test by hand. However, they are adapted to the natural swelling movement of the wound.

In the case of a greatly swelling wound—for example caused by inflammation—it is advisable to use a somewhat more extensible plaster than in the case of a wound which shows less swelling, in order to obtain the most satisfactory closure of the wound.

Although appropriate knitted and woven fabrics, nonwovens or sheets are suitable in principle as the carrier material, a knitted fabric is preferably used.

Such elastic knitted fabrics car consist, for example, of nylon, polyester or polyurethane/staple rayon yarns. A knitted nylon fabric of high tear strength is preferred.

The carrier material is provided in the known manner with a microporous self-adhesive layer, in order to ensure good air permeability and water vapour permeability. When the preferred knitted fabric is used, particularly good values result because of the comparatively large pores in the carrier, namely an air permeability of at least 10 cm$^3$/cm$^2$ sec and a water vapour permeability of at least 700 g/m$^2$. As adhesive compositions which are well tolerated by the skin and have high tack, those consisting of polyacrylic acid esters or acrylic acid ester copolymers, in particular according to German Patent Specification No. 2,743,979, have proved suitable.

In the industrial procedure for the manufacture of the wound suture plasters according to the invention, the adhesive composition is spread, preferably as a solution, on a temporary support with a non-stick finish, for example siliconized kraft paper, and dried by rapid evaporation of the solvent at elevated temperature to give a form with fine blisters. After cooling to room temperature, the actual carrier material is laminated to the adhesive layer and, if necessary, subjected to a calendering step according to German Patent No. 1,569,901. As a result, the adhesive composition is transferred to the carrier material and the fine blisters are broken open, whereby a fine-pored microporous structure is produced. If required by the adhesive composition, a crosslinking process by action of heat or UV irradiation can also follow.

The product is then made up for use, that is to say cut into strips of desired length and width, relaminated to to the final auxiliary support with spacings between the individual strips, sealed in to be microbiologically impervious and sterilized by gamma-radiation.

The wound suture plasters according to the invention, produced in this way, with a reversible elastic carrier material meet all the requirements in practice. They are so supple and flexible that they adapt themselves to the irregularities of the skin but are at the same time so extensible, resilient and tear-resistant that the edges of the wound are firmly held together at any time without tissue damage. This means reliable adaptation of the edges of the wound, until the scar has built up sufficient strength of its own.

The examples which follow are intended to explain the production of the novel wound suture plasters in more detail:

EXAMPLE 1

A self-adhesive composition, obtained by copolymerization of 49 parts by weight of 2-ethylhexyl acrylate, 49 parts by weight of n-butyl acrylate and 2 parts by weight of glycidyl methacrylate, is applied from a solution in an acetone/petroleum ether mixture to a siliconized release paper in such a quantity that, after drying, a layer thickness of about 50 g/m² is obtained. For rapid evaporation of the solvent mixture, the release paper coated with the adhesive composition is then passed through a drying channel heated stage-wise to temperatures of 60°-100° C., whereby a multiplicity of tiny blisters forms in the adhesive layer. After cooling to room temperature, a knitted nylon 6,6 fabric having the following data is laminated to the dried adhesive layer:

|  | Wales | Courses |
|---|---|---|
| Thread density (threads/cm): | about 12 | about 21 |
| Yarn count (dtex): | 44 | 44 |
| Breaking strength (N/cm): | about 55 | about 130 |
| Elongation at break (%): | about 50 | about 70 |
| Weight per unit area: | about 75 g/m² | |

The composite product is then calendered under a pressure of about 5 kp/cm². After this calendering step, during which the small blisters break open and simultaneously the adhesive layer bonds itself firmly to the knitted fabric, the wide rolls are cut up into narrow rolls of varying widths, the still adhering release paper is pulled off and the cut ribbons, in sections of 10cm length each and several side by side, are placed again onto a siliconized release paper. After packaging, the finished wound suture plasters are subjected to gamma-radiation (2.5 Mrad absorbed dose) and sterilized in this manner. At the same time, the adhesive composition undergoes further crosslinking which improves its cohesion in a desirable manner.

EXAMPLE 2

A knitted nylon fabric carrier material as described in Example 1 is provided with a layer of a UV-crosslinkable self-adhesive composition according to German Patent No. 2,743,979. The procedure followed here is essentially as in the preceding Example 1, but a copolymer of 73.59% by weight of 2-ethylhexyl acrylate, 20% by weight of butyl acrylate, 6% by weight acrylic acid and 0.41% by weight of benzoin acrylate is used.

After the release paper carrying the dried self-adhesive layer and the fabric carrier have been laminated together, the composite product is irradiated from the fabric side for about one second with 4×11-12 kW UV-radiation in order to crosslink the adhesive composition. The further processing and making-up is carried out analogously to Example 1. The product shows particularly good tack.

Extension measurements on this product, using a tensile testing machine, gave the following values at pulling forces of 5, 10 and 20 N/cm:

Between about 4 and 10% at 5 N/cm,
Between about 6 and 14% at 10 N/cm and
Between about 17 and 30% at 20 N/cm, measured on strips of varying widths (0.4–2.6 cm) of different charges of material, at varying pulling rates (20, 100,and 300 mm/minute) and varying clamping lengths (20, 50, 60 and 100 mm). The extension was reversible in virtually every case, that is to say, after tension release, the strips reassumed the original length. Occasional slight residual values result, inter alia, from the fact that the material is never completely homogeneous.

We claim:

1. A self-adhesive wound suture plaster in strip form consisting essentially of an elastic carrier material carrying an adhesive, the carrier strip extending under the action of a pulling force and, after this action of force has ended, virtually returning completely to its original length, the carrier strip undergoing a length extension of between about 1 and 15% under the action of a pulling force of 5 N/cm.

2. A wound suture plaster according to claim 1, wherein the carrier strip undergoes a length extension of between about 2 and 20% under the action of a pulling force of 10 N/cm and a length extension of between about 6 and 35% at 20 N/cm.

3. A wound suture plaster according to claim 1, wherein the carrier strip undergoes a length extension of between about 2 and 10% under the action of a pulling force of 5 N/cm, a length extension of between about 5 and 15% at 10 N/cm and a length extension of between about 15 and 30% at 20 N/cm.

4. A wound suture plaster according to claim 1, wherein the carrier material consists of an elastic knitted fabric.

5. A wound suture plaster according to claim 1, wherein the carrier material consists of an elastic knitted nylon fabric.

6. A wound suture plaster according to claim 1, having an air permeability of at least 10 cm³/cm² sec and a water vapour permeability of at least 700 g/m².

* * * * *